(12) United States Patent
Goldammer et al.

(10) Patent No.: US 9,263,164 B2
(45) Date of Patent: *Feb. 16, 2016

(54) METHOD AND DEVICE FOR CORRECTING ARTEFACTS DURING X-RAY IMAGERY, ESPECIALLY COMPUTER TOMOGRAPHY, WITH A MOVING MODULATOR FIELD

(75) Inventors: Matthias Goldammer, München (DE); Karsten Schörner, München (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 168 days.

This patent is subject to a terminal disclaimer.

(21) Appl. No.: 14/009,189
(22) PCT Filed: Mar. 23, 2012
(86) PCT No.: PCT/EP2012/055203
§ 371 (c)(1),
(2), (4) Date: Oct. 1, 2013
(87) PCT Pub. No.: WO2012/130755
PCT Pub. Date: Oct. 4, 2012

(65) Prior Publication Data
US 2014/0146935 A1    May 29, 2014

(30) Foreign Application Priority Data
Apr. 1, 2011 (DE) .......................... 10 2011 006 660

(51) Int. Cl.
*G21K 1/10* (2006.01)
*A61B 6/00* (2006.01)
(Continued)

(52) U.S. Cl.
CPC ................ *G21K 1/10* (2013.01); *A61B 6/4035* (2013.01); *G01N 23/046* (2013.01); *G06T 5/002* (2013.01);
(Continued)

(58) Field of Classification Search
CPC ........ A61B 6/483; A61B 6/032; A61B 6/482; A61B 6/5258; A61B 6/5282; A61B 6/4035; A61B 6/405; G06T 1/1005; G01N 23/04; G21K 1/10

USPC .......................... 378/6, 7, 62, 98.4, 156, 158
See application file for complete search history.

(56) References Cited

U.S. PATENT DOCUMENTS

| 5,533,088 | A | 7/1996 | Fivez |
| 7,463,712 | B2 | 12/2008 | Zhu et al. |
| 8,989,469 | B2 * | 3/2015 | Fahimian ............... A61B 6/032 378/19 |

FOREIGN PATENT DOCUMENTS

| DE | 2454537 | 5/1976 |
| DE | 102011006660.8 | 4/2011 |
| EP | PCT/EP2012/055203 | 3/2012 |

OTHER PUBLICATIONS

Jing Wang et al., "Scatter correction for cone-beam computed tomography using moving blocker strips: A preliminary study," Medical Physics 37 (11), Nov. 2010, pp. 5792-5800.
(Continued)

*Primary Examiner* — Jurie Yun
(74) *Attorney, Agent, or Firm* — Staas & Halsey LLP

(57) ABSTRACT

A method and a device produce X-ray images of objects, according to which artifacts caused by scattered radiation are corrected. To this end, a modulator field is used, that can be moved from a first position to a second position, thereby enabling modulator field areas with small and relatively large X-ray attenuation coefficients to be interchanged. An initial amplitude-modulated projection of the object is respectively produced in each of the two positions, and a scattered image associated with the projection is respectively calculated. This is especially suitable for rapid CT scans.

23 Claims, 8 Drawing Sheets

(51) Int. Cl.
  *G01N 23/04* (2006.01)
  *G06T 11/00* (2006.01)
  *G06T 5/00* (2006.01)
  *G06T 5/50* (2006.01)
  *A61B 6/03* (2006.01)

(52) U.S. Cl.
  CPC ............... *G06T 5/50* (2013.01); *G06T 11/005* (2013.01); *A61B 6/03* (2013.01); *A61B 6/4085* (2013.01); *A61B 6/5282* (2013.01); *G01N 2223/419* (2013.01); *G06T 2207/10116* (2013.01); *G06T 2207/10144* (2013.01); *G06T 2207/30004* (2013.01)

(56) References Cited

OTHER PUBLICATIONS

Lei Zhu et al., "X-ray scatter correction for cone-beam CT using moving blocker array," Proceedings of SPIE, vol. 5745 (2005), pp. 251-258.

Jian-Yue Jin et al., "Combining scatter reduction and correction to improve image quality in cone-beam computed tomography (CBCT)," Medical Physics 37 (11), Nov. 2010, pp. 5634-5644.

Peter Hammersberg et al., "Correction for beam hardening artefacts in computerised tomography," Journal of X-Ray Science and Technology 8, 1998, pp. 75-93.

G. Kowalski, "Suppression of scattered radiation in radiography and improvement of resolution by spatially modulated intensity," Applied Optics, vol. 15, No. 3, Mar. 1976, pp. 648-655.

Hewei Gao et al., "Scatter correction method for x-ray CT using primary modulation: Phantom studies," Medical Physics, vol. 37, No. 2, Feb. 2010, pp. 934-946.

German Office Action for German Priority Patent Application No. 10 2011 006 660.8, issued Jan. 26, 2012, 7 pages.

English language International Search Report for PCT/EP2012/055203, mailed Jul. 9, 2012, 3 pages.

English language translation of Written Opinion for PCT/EP2012/055203, downloaded from WIPO website Oct. 1, 2013, 6 pages.

* cited by examiner

METHOD AND DEVICE FOR CORRECTING ARTEFACTS DURING X-RAY IMAGERY, ESPECIALLY COMPUTER TOMOGRAPHY, WITH A MOVING MODULATOR FIELD

CROSS REFERENCE TO RELATED APPLICATIONS

This application is based on and hereby claims priority to International Application No. PCT/EP2012/055203 filed on Mar. 23, 2012 and German Application No. 10 2011 006 660.8 filed on Apr. 1, 2011, the contents of which are hereby incorporated by reference.

BACKGROUND

The present invention relates to a method and device that correct artifacts.

In industrial computed tomography (CT), scatter radiation also occurs in addition to the primary radiation that is to be detected. If nothing is done to prevent the detection of scatter radiation or if the recorded projections remain uncorrected, this leads to scatter radiation artifacts in the reconstructed CT volume composed of voxels. Scatter radiation artifacts of said type can be caused for example as a result of what is called a cupping effect which leads to inhomogeneous voxel values in a homogeneous object material, such that when the density values are plotted along a line, in other words when a line profile is produced, a curve results instead of a straight line. Generally, streak patterns and contrast losses can be produced in addition.

Different conventional solution approaches to scatter radiation correction exist which can mainly be classified into two groups:

1. Measures to reduce the detected scatter radiation, as implemented for example through the use of an anti-scatter grid.

2. So-called a posteriori corrections of the scatter radiation, whereby the scatter component in each CT projection is subtracted accordingly.

A maximally precise knowledge of the detected scatter component is necessary for the second group. Toward that end various approaches for determining said scatter component exist, which can likewise be divided into two groups:

1. Software-based solutions, such as Monte Carlo simulations, deterministic calculations of first-order scatter, convolution algorithms based on what are known as point spread functions, for example.

2. Experimental methods for determining the scatter component with the aid of measurements.

Within this second group of experimental methods, different measurement methods are known. For example:

a) beam-stopper-based methods, and b) a complementary technique thereto, which uses apertures and moreover so-called beam holes, and c) an only recently proposed method which is based on what is termed primary modulation.

With regard to the last-cited method, the following related art is known.

U.S. Pat. No. 7,463,712 B2 discloses a scatter correction method for x-ray imaging, wherein a direction-dependent modulation of the primary x-ray radiation is used, leading to a space-dependent modulation on the primary radiation detector. Scatter radiation in an x-ray imaging system including an x-ray source and an x-ray detector is corrected by using amplitude modulation to translate the spatial frequency of a detected x-ray beam to a higher frequency and by filtering out the low-frequency scatter radiation. A measure for the low-frequency primary signal without scatter radiation is then obtained by demodulating the detected modulated signal.

The decisive advantage of a method using primary modulation over other conventional experimental methods is that the scatter measurement and scatter beam estimation can be carried out during the actual CT scan, i.e. the scatter data is acquired simultaneously with the actual CT projections. Compared with other conventional methods that require an additional measurement operation, this results in a smaller measurement overhead and at the same time realizes a time saving, which represents a critical advantage in particular for industrial CT. Furthermore, savings in terms of radiation dose are also achieved compared to measurement methods in which an additional measurement operation is required.

The conventional method according to U.S. Pat. No. 7,463,712 B2 provides that a primary modulator is placed between the object that is to be imaged and the x-ray tube. The primary modulator impresses a pattern, for example in the form of a checkerboard composed of light and dark fields, on the primary beams by amplitude modulation. For that purpose a printed circuit board made of copper for example can be used, into which a pattern is introduced by etching processes, i.e. the copper is correspondingly etched away on the light fields. The different strengths of the attenuation properties or attenuation coefficients of copper and of the bare printed circuit board material ensure a corresponding beam attenuation through the dark fields (copper), while there is hardly any attenuation or none at all on the light fields (printed circuit board material). Throughout the entire CT scan or the entire CT sampling the modulator remains stationary between object and x-ray tube, i.e. it does not change its position. The modulated checkerboard-like pattern is therefore to be found again in every projection of the CT scan, i.e. both in free beam regions and in object-covered regions. In this case the relative modulation strength, insofar as the primary signal is concerned, is equally great at all points. However, not just this modulated primary signal is recorded by the detector, but in addition, superimposed on said signal, is a low-frequency scatter signal which results due to x-ray scatter effects, in particular Compton scatter processes, in the test object and in the laboratory environment. The detector therefore records an overall signal formed of the modulated primary signal and the superimposed unmodulated scatter signal.

Subsequently it is possible to separate the modulated primary signal from the unmodulated scatter signal in the Fourier domain. This is accomplished by corresponding high-pass or low-pass filtering of the modulated projection. The low-pass filtered version of the modulated projection results in the overlapping of the frequency components of unmodulated primary image and scatter function in the frequency domain. The high-pass filtered version contains only the spectral component of the modulated primary signal, in other words it can subsequently be demodulated and weighted in order to obtain an approximation of the exclusive primary signal in the frequency domain. Following an inverse Fourier transform this can be subtracted as an approximated primary image from the low-pass filtered version, which includes scatter and primary signals, in order to obtain an approximation of the scatter image. It is pointed out that in the method described herewith so-called edge detection and edge smoothing, also referred to as boundary detection, is applied to every modulated projection. Smoothing of said kind takes into account that high-frequency image components are already present due to the object alone and in particular due to the object edges. This is independent of any modulation. Said unmodulated high-frequency components overlap in the Fourier domain with the spectral copies of the modulated primary signal. Mixing modulated and unmodulated signal will, if the latter is not corrected, result in incorrect demodulation of the primary signals. In other words, artifacts will be produced especially in the object edge regions and also in the inside of the object, which is then referred to in this context as "spilling", leading to incorrect reconstruction of the primary image. In order to attenuate or suppress such high-frequency image components, which are caused in particular by object edges, the above-cited boundary detection is applied in order to find the object edges and smooth the same accordingly by a Gaussian filter.

Although the strong artifacts caused by excessively high-frequency, unmodulated image components are reduced in this process, an inaccuracy in the edge region is produced at such points, since the Gaussian filtering is no longer reversed subsequently. The thus obtained scatter image is now subtracted accordingly from the CT projections. Since the modulation pattern is still now present in the projections, the CT projections are normalized to the radiation intensity after the modulator. In this way the modulator pattern is removed in the projection image. This is accomplished by division by a recording of the modulator without further objects in the beam path. It is pointed out that beam hardening effects are produced due to the modulator, and moreover these are caused in particular by the dark copper fields. If such effects remain uncorrected, the result is firstly an inaccurate scatter estimation and secondly an incomplete removal of the checkerboard pattern in the last-cited division step. This can lead to ring artifacts in the CT cross-sectional images. The fact that beam hardening effects exist and lead to the cited errors is known for example from "Correction for beam hardening artifacts in computerized tomography," by Hammersberg et al. (Journal of X-Ray Science and Technoglogy 8, 1998).

Hammersberg et al. discloses that when polyenergetic x-ray sources are used, accurate density measurements are made more difficult due to beam hardening based on incorrect gradients of linear attenuation coefficients in computed tomography cross-sectional images. A correction method is described in which polyenergetic computed tomography data is converted into monoenergetic computed tomography data by linearization. Computed tomography data is derived from measured data points as a function of the object thickness and represented as a polynomial. Using simulations, the polyenergetic computed tomography data is accurately simulated on the basis of the object material density, the object material composition, the x-ray energy spectrum, the detector response, and the information transfer from the detector to digitized data. The curve of the function representing the polyenergetic computed tomography data can be accurately determined by an eighth- or higher-order polynomial or by cubic spline interpolation.

SUMMARY

One potential object is to provide a method and a device for x-ray imaging, in particular computed tomography, or digital radiography such that artifacts generated due to scatter radiation can be corrected in a reconstructed computed tomography volume more easily and effectively in comparison with the related art. Artifacts of such kind can be for example cupping effects, streak patterns and/or contrast losses. Furthermore, an artifact due to beam hardening caused as a result of a primary modulation is also intended to be easily and effectively corrected. It is aimed for example to achieve an improvement in contrast compared to conventional methods.

The inventors propose a method for correcting artifacts in an x-ray projection of an object, wherein x-ray radiation of a primary x-ray source passes through a modulator field having a repetitive pattern of areas exhibiting different x-ray radiation attenuation, is amplitude-modulated thereby, then passes through the object that is to be imaged to a detector, where it is recorded and a scatter image is calculated therefrom which is separated from an original amplitude-modulated projection. The method is characterized in that the modulator field is moved from a first position to a second position and as a result modulator field areas with a small x-ray radiation attenuation coefficient and by comparison therewith a relatively large x-ray radiation attenuation coefficient are reciprocally interchanged, an original amplitude-modulated projection of the object is generated in each case in each of the two positions, and a scatter image associated with the projection is calculated in each case.

According to a second aspect, a device for correcting artifacts in an x-ray projection of an object is provided, wherein x-ray radiation of a primary x-ray source passes through a modulator field having a repetitive pattern of areas exhibiting different x-ray radiation attenuation, is amplitude-modulated thereby, then passes through the object that is to be imaged to a detector, where it is recorded and a scatter image is calculated therefrom which is separated from an original amplitude-modulated projection, wherein the modulator field has a repeating pattern, the first half of which is congruent with a second half, mutually congruent areas of the two halves have mutually opposite x-ray radiation attenuation coefficients, the pattern is repeated along at least one repetition line, and a length of the pattern along the repetition line corresponds to a period length. The device is characterized in that a shifting apparatus for moving the modulator field from a first position to a second position along the repetition line displaces the modulator field by an uneven multiple of a half period length in each case such that modulator field areas with a small x-ray radiation attenuation coefficient and by comparison therewith a relatively large x-ray radiation attenuation coefficient are reciprocally interchanged.

A modulator field acting as a primary modulator extends along a plane and has thicknesses corresponding to the modulator material.

By opposite x-ray radiation attenuation coefficients is meant for example on the one hand a large x-ray radiation attenuation coefficient and by comparison therewith a relatively small x-ray radiation attenuation coefficient. A value range of normalized x-ray radiation attenuation coefficients is determined in that these values can be in particular greater than or equal to zero and less than or equal to one.

Projection image fields are produced which were generated by radiation passing through areas of the modulator field having the relatively small x-ray radiation attenuation coefficient, which can be described as light fields. Projection image fields which were generated by radiation passing through areas of the modulator field having the relatively large x-ray radiation attenuation coefficient can be described as dark fields.

A repetition line of the pattern of the modulator field is a line along which the pattern is repeated. A length of a repetition line in a pattern corresponds to a period length. A repetition line can be a straight line.

Advantageously, ring artifacts generated due to dark grid fields in a static primary modulator can be effectively reduced according to the proposed solution.

According to the inventors' proposals, a modulator-free or an approximated modulator-free overall image can be generated and used to divide out high-frequency image components from a modulated projection. In this way a much more accurate scatter estimation is possible by comparison with the related art, and moreover in particular in the region of the object edges and in proximity to high-contrast object details. Inside of the object, too, a division of said kind leads to improvements compared with the above-described related art. Furthermore, a moving primary modulator has the great advantage compared to a stationary primary modulator that any not fully compensated residual patterns of the primary modulator will be evenly distributed over the entire volume or over a CT cross-section in a backprojection process of the reconstruction. Typical ring artifacts, such as occur with a stationary modulator, are avoided in this way. Equally, this makes a subsequent use of algorithms in order to suppress ring artifacts, as described according to U.S. Pat. No. 7,463,712 B2, merely optional.

According to an advantageous embodiment, in order to calculate a scatter image associated with a projection, a modulator-free overall image can be constructed by combining the two original projections of the object, with only projection image fields being used that were generated by radiation passing through areas of the modulator field having the relatively small x-ray radiation attenuation coefficient.

According to another advantageous embodiment, in order to calculate a scatter image associated with a projection, a subsampling step is performed before the modulator-free overall image is calculated. The technical term used to describe such a subsampling step is "downsampling".

According to another advantageous embodiment, in order to calculate a scatter image associated with a projection, high image frequencies caused due to high-contrast object details can be removed from the respective modulated projection by division of a respective downsampled amplitude-modulated projection by the modulator-free overall image.

According to another advantageous embodiment, in order to calculate a scatter image associated with a projection, the respective amplitude-modulated projection can be high-pass filtered in the frequency domain in order to remove a low-frequency scatter signal component, demodulated in the space domain by multiplication of a modulator field projection without object and then low-pass filtered, and thereafter multiplied by the modulator-free overall image in order to provide a demodulated primary image associated with a projection.

According to another advantageous embodiment, in order to calculate a scatter image associated with a projection, the demodulated primary image associated with the projection can be subtracted from the modulator-free overall image.

According to another advantageous embodiment, in order to provide a scatter-corrected projection, the scatter image associated with the projection can be subtracted from the associated original, non-downsampled projection.

According to another advantageous embodiment, in order to provide an additionally modulator-field-corrected projection, the scatter-corrected projection can be divided by the modulator field projection without object.

According to another advantageous embodiment, a scatter-corrected or scatter- and modulator-field-corrected projection can be generated in each case for the first and the second position of the modulator field, wherein a signal-to-noise ratio can be increased by subsequent averaging.

According to another advantageous embodiment, the modulator field can be moved back and forth between the first and second position and after every second projection the object can be rotated about an axis of rotation in one rotational direction by a rotation angle increment.

According to another advantageous embodiment, the modulator field can be moved back and forth between the first and second position and after every projection the object can be rotated about an axis of rotation in one rotational direction by a rotation angle increment, wherein in order to calculate a scatter image associated with a projection, instead of a modulator-free overall image, an approximated modulator-free overall image is used in which projection image fields of a current original projection of the object are combined with interpolated projection image fields of a preceding and a succeeding original projection of the object, with only projection image fields being used that were generated by radiation passing through areas of the modulator field having the relatively small x-ray radiation attenuation coefficient.

According to another advantageous embodiment, for beam hardening correction, for a projection image field that was generated by radiation passing through an area of the modulator field having the relatively large x-ray radiation attenuation coefficient, an approximated scatter value can be subtracted in each case from a measured uncorrected intensity value, this difference corresponding to a first intensity value which can be assigned by an associated intensity attenuation curve to an associated radiation-penetrated object depth, this can be assigned by an intensity attenuation curve for a projection image field that was generated by radiation passing through an area of the modulator field having the relatively small x-ray radiation attenuation coefficient to a second intensity value to which the approximated scatter value can be added again.

According to another advantageous embodiment, the approximated scatter value can be determined from a calculated scatter image of a preceding original projection.

According to another advantageous embodiment, the beam hardening correction can be carried out during a downsampling step. In this way scatter estimation, in particular for monomaterials, can be significantly improved.

According to another advantageous embodiment, the beam hardening correction can be carried out prior to the division of the scatter-corrected projection by the modulator field projection without object. This advantageously effects a more complete correction of the modulator field pattern in the division step by the modulator projection, as a result of which ring artifacts in the CT volume can in turn be reduced.

According to another advantageous embodiment, the device can be a computed tomography system.

According to another advantageous embodiment, the computed tomography system can be a cone-beam computed tomography system.

According to another advantageous embodiment, the computed tomography system can be a cone-beam computed tomography system for industrial applications.

According to another advantageous embodiment, the shifting apparatus and a rotation apparatus for rotating the object about an axis of rotation in one rotational direction by respective rotation angle increments can be synchronized with one another.

According to another advantageous embodiment, the pattern of the modulator field can be a checkerboard pattern.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
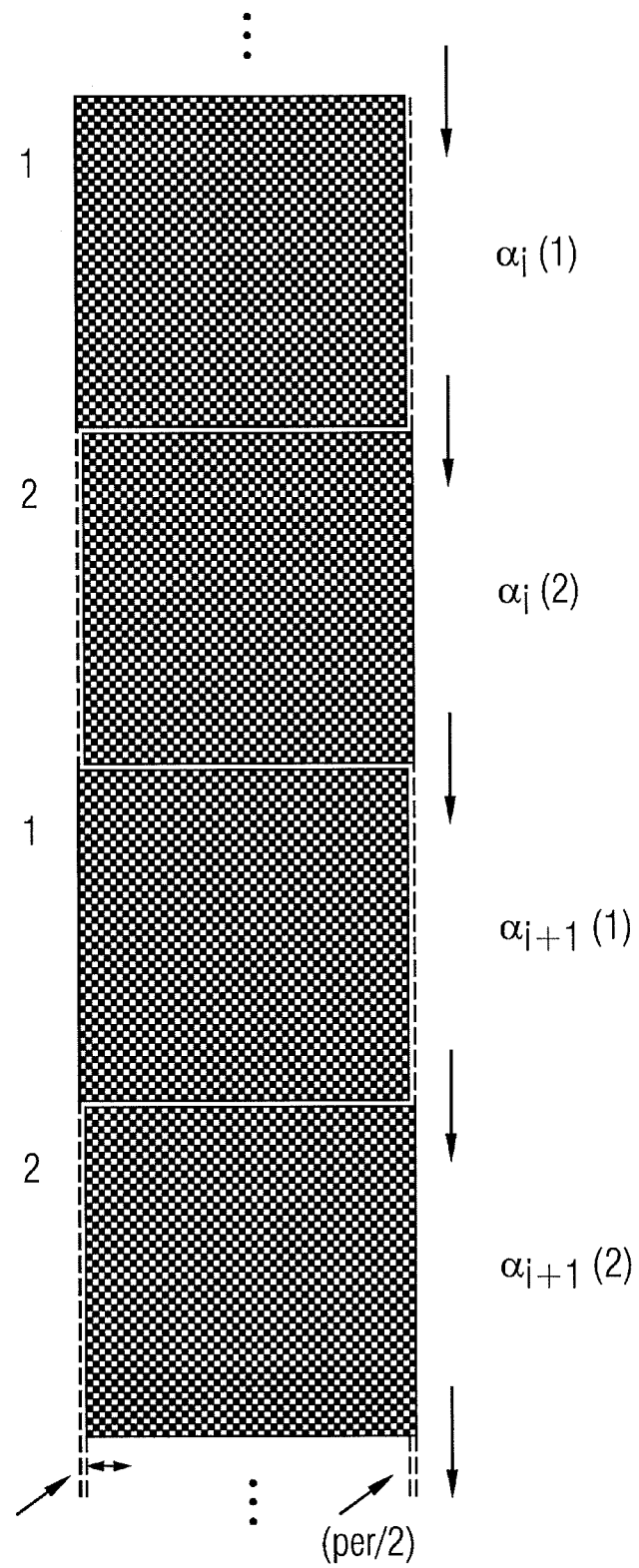
FIG. 1 shows an exemplary embodiment of a modulator field movement and object movement relative thereto.

Reference will now be made in detail to the preferred embodiments of the present invention, examples of which are illustrated in the accompanying drawings, wherein like reference numerals refer to like elements throughout.

FIG. 1 shows an exemplary embodiment of a modulator field movement and an object movement relative thereto; a movement or, as the case may be, an offset, which for example can be horizontal or vertical or diagonal, of the primarily modulating modulator field by half a period length per/2 is provided, and moreover in such a way that two projections with modulator field offset by per/2 are present for each angular position of the object that is to be tomographed. For that purpose the modulator field is not installed in a stationary manner, as disclosed according to U.S. Pat. No. 7,463,712 B2, but is provided on a motorized linear stage so as to be movable by at least half a period length. During a CT scan, the modulator field is then displaced by half a period length for each angular position $\alpha_i$ (i=1 ... n, where n signifies the number of angular positions to be recorded) of the object that is to be tomographed after a first projection recording in a first modulator position 1 (projection $\alpha_i(1)$) in such a way that in the case of a checkerboard-like modulator field the dark fields come to lie where previously there were light fields, and vice versa. A second projection is then recorded (at the second modulator position 2 (projection $\alpha_i(2)$), with the object that is to be tomographed not yet having been moved. For the next angular position $\alpha_{i+1}$ of the object to be tomographed and all following positions, this twofold recording procedure with the first modulator field position 1 and the second modulator field position 2 is repeated in the same way. The vertical arrows are equivalent to a time bar.

Figure 2:
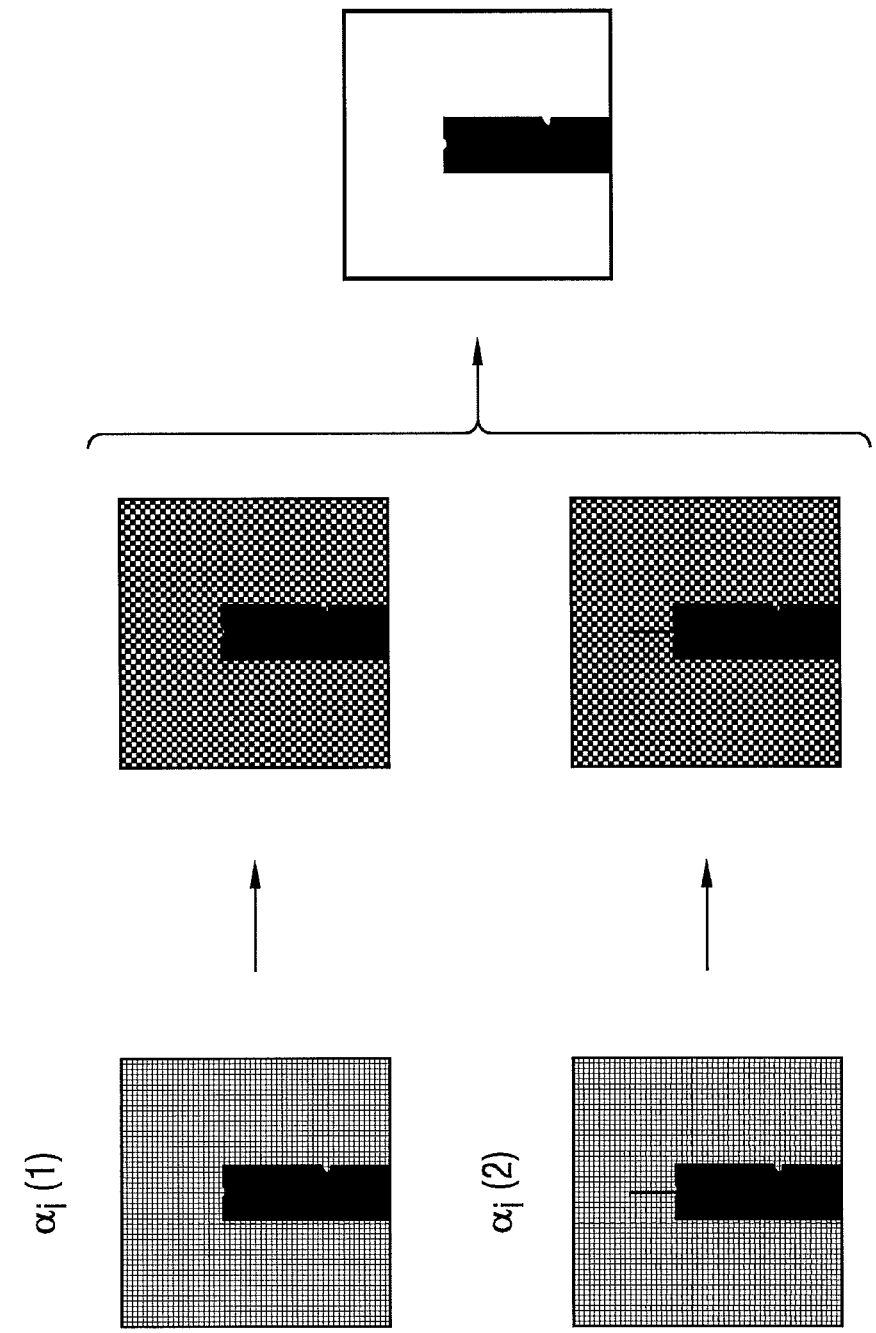
FIG. 2 shows a first exemplary embodiment of a construction of a modulator-free overall image.

FIG. 2 shows a first exemplary embodiment of a construction of a modulator-free overall image. By the offset by half a period length between the two modulator positions 1 and 2 it is possible in the proposed method to construct a modulator-free overall image for each angular position $\alpha_i$ of the object that is to be tomographed, said overall image being in particular downsampled. This is illustrated in FIG. 2. Toward that end, the light fields from the first projection $\alpha_i(1)$ are transferred into a new image, in particular after a downsampling step. The dark fields from said projection cannot be used, and must therefore be replaced in order to generate a modulator-free image. As a result of the offset by half a period, however, light fields are located in the second projection, i.e. projection $\alpha_i(2)$, at those positions where dark fields are to be found in the first projection $\alpha_i(1)$. Said light fields are likewise transferred into the new image, and moreover in particular after the downsampling step, thereby resulting in the modulator-free overall image.

Figure 3:
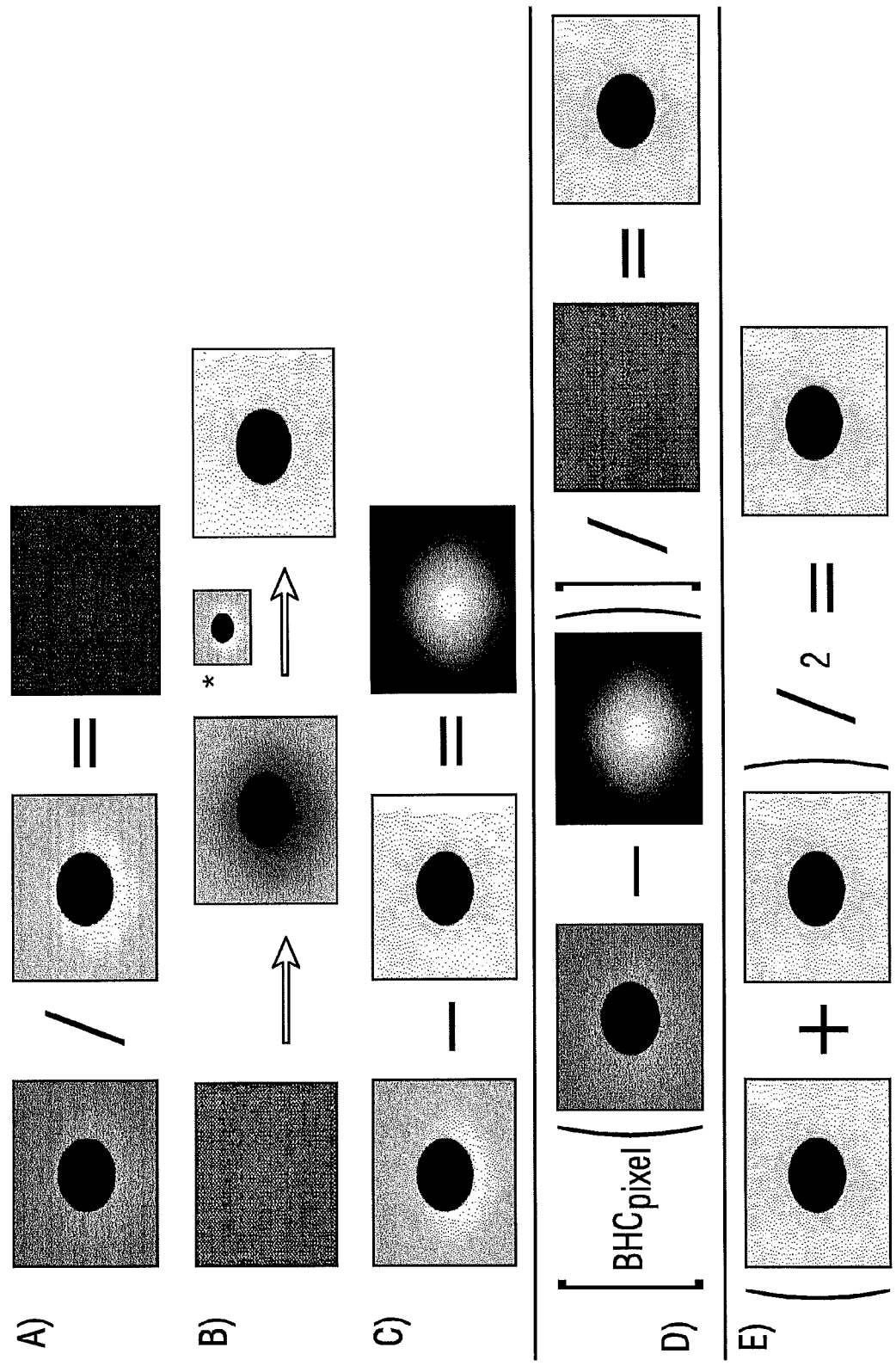
FIGS. 3A to 3E show an exemplary embodiment of a proposed method for providing a scatter-corrected projection.

FIGS. 3A to 3E show an exemplary embodiment of the proposed method for providing a scatter-corrected projection. With the modulator-free overall image, the high image frequencies caused by object edges and other high-contrast object details can subsequently be divided out. This is illustrated in FIG. 3A. The modulated projection image, which is in particular downsampled, is therefore divided by the modulator-free overall image, which is in particular downsampled, resulting in the ratio of measured modulation strength of the primary signal to the overall signal strength. A division of said type by the modulator-free overall image replaces the "boundary detection" step of U.S. Pat. No. 7,463,712 B2.

This modulation image freed of object image frequencies is then high-pass filtered in the Fourier domain, thereby removing the low-frequency scatter component. Next there follows a demodulation by multiplication in the space domain by a modulator projection without sample. This is illustrated in FIG. 3B. The previously performed division by the modulator-free overall image, which is in particular downsampled, is reversed after the demodulation step by a corresponding multiplication of the in particular downsampled modulator-free overall image by the reconstructed primary image. This is illustrated in FIG. 3B.

FIG. 3C shows how subsequently the modulator-free overall image is likewise used in order to generate the scatter image by subtraction of the reconstructed primary image.

FIG. 3D shows how the calculated scatter image is subsequently subtracted from the original modulated CT projection, which is in particular not downsampled. Then follows a pixel-by-pixel beam hardening correction, which is represented as operation BHC [.] in FIG. 3D and is described in greater detail in conjunction with FIG. 7. Finally, in order to rectify the modulator pattern, the scatter-and beam-hardening-corrected image can be divided by a pure modulator projection, i.e. without object in the beam path.

The steps described hereintofore, as illustrated in FIGS. 3A to 3D, are performed for both projections $\alpha_i(1)$ and $\alpha_i(2)$ in the first modulator position 1 and the second modulator position 2. As the object was not moved in these two projections, the scatter-, beam-hardening-and modulator-corrected projections, which are in each case the results of step 3D, are averaged in order to improve the signal-to-noise ratio (SNR). This is illustrated in FIG. 3E.

Figure 4:
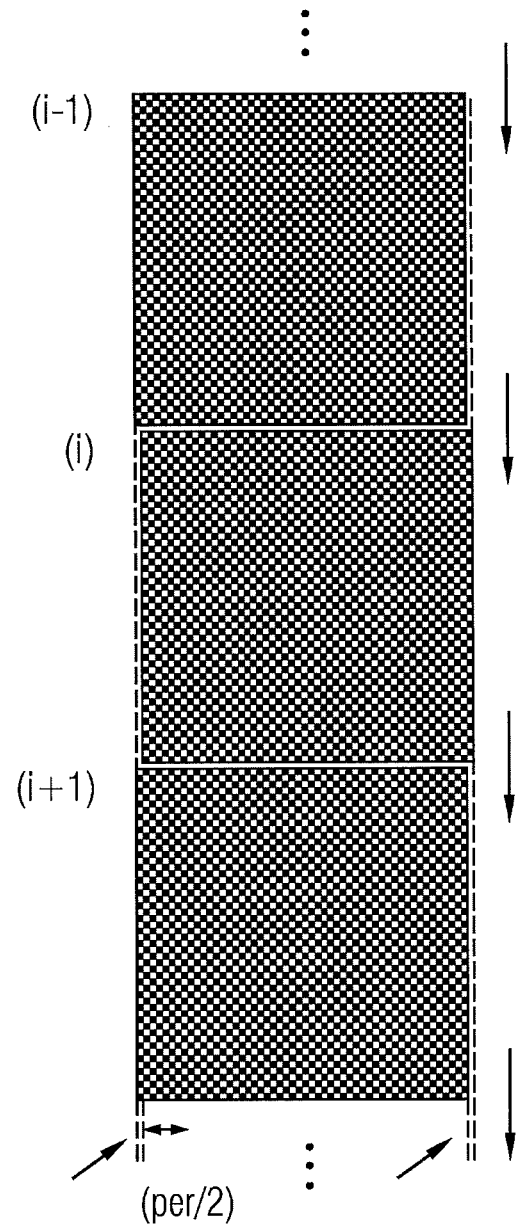
FIG. 4 shows a second exemplary embodiment of a modulator field movement and an object movement relative thereto.

FIG. 4 shows a second exemplary embodiment of a modulator field movement and an object movement relative thereto. FIG. 4 represents a second alternative of an offset of a primarily modulating modulator field. In this case an offset can be executed for example horizontally or vertically. Other displacement directions are also possible. For example, the modulator field pattern can have been generated in such a way that an offset can be executed diagonally. According to this second exemplary embodiment, the primary modulator is offset by half a period length per/2 from projection to projection, between which in each case an angle rotation increment of the object that is to be tomographed is carried out. Toward that end the modulator field is not installed in a stationary manner, but is provided on a motorized linear stage to allow movability by at least half a period length. During a CT scan, the modulator field is then displaced as the primary modulator by half a period length from projection to projection in such a way that in the case of a checkerboard-like pattern of the modulator field the dark fields come to lie where previously there were light fields, and vice versa. This is illustrated in FIG. 4. The vertical arrows are equivalent to a time bar according to FIG. 1.

Figure 5:
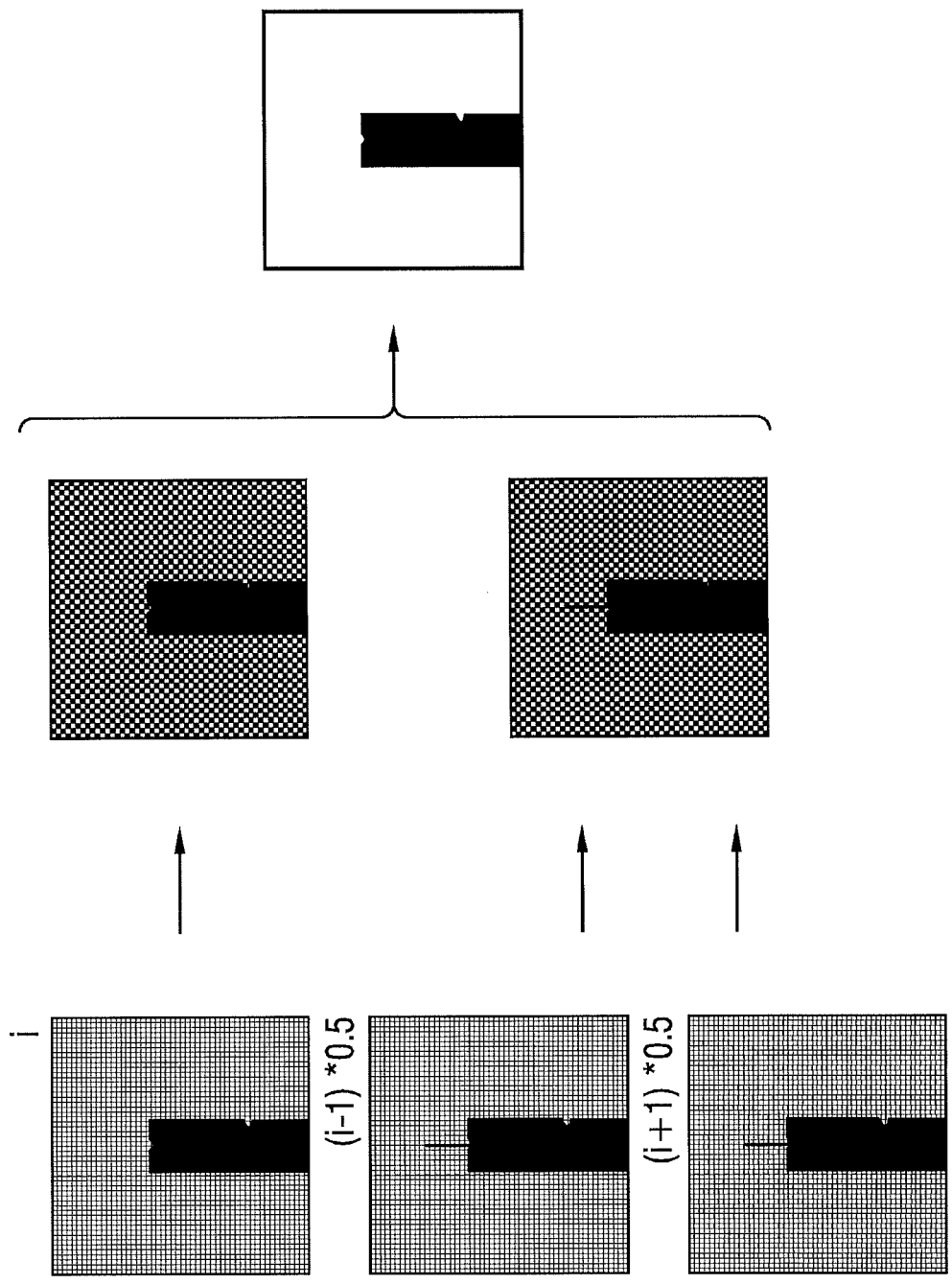
FIG. 5 shows a second exemplary embodiment of a construction of an approximated modulator-free overall image.

As a result of the offset by half a period length from projection to projection it is possible according to the exemplary embodiment to construct an approximated modulator-free overall image for each projection. This is illustrated in FIG. 5. Toward that end the light fields from the current projection, designated as projection i, are transferred into a new image, and moreover in particular after the downsampling step. The dark fields from said projection i cannot be used, and must therefore be replaced in order to generate a modulator-free image. As a result of the offset by half a period, however, light fields are located in the preceding projection (i−1) and in the succeeding projection (i+1) at those positions where dark fields are to be found in the current projection i. By a simple interpolation, approximated grayscale value signals can be found for said fields; depending on object composition and increment size of the sample or object rotation angle, these grayscale value signals represent a very good approximation to the actual grayscale value signals which, though, have not been measured here. An interpolation can be provided for example by a uniform weighting in the case of neighboring projections, for example with an equal weighting of 0.5.

FIG. 5 shows a second exemplary embodiment of a construction of an approximated modulator-free overall image. In this case the modulator-free overall image is merely approximated. According to this embodiment variant, each time a modulator field is offset or shifted by half a period length between the two modulator positions 1 and 2, an angular position $\alpha_i$ of the object to be tomographed is changed, with the result that on this basis a modulator-free overall image, which is in particular downsampled, can only be approximated. This is illustrated in FIG. 5. Toward that end the light fields from a current projection (i) are transferred into a new image, in particular after a downsampling step. The dark fields from this projection cannot be used, and must therefore be replaced in order to approximate a modulator-free image. As a result of the offset by half a period, however, light fields are located in a preceding projection (i−1) where dark fields are to be found in the current projection (i). In a following projection (i+1) light fields are likewise located where dark fields are to be found in the current projection (i). The preceding and succeeding projections can be combined and weighted relative to each other, for example by a factor of 0.5 in each case. These light fields of the three projections (i−1, i, i+1) are transferred into the new image, and moreover in particular after the downsampling step, thereby producing the approximated modulator-free overall image as result.

Figure 6:
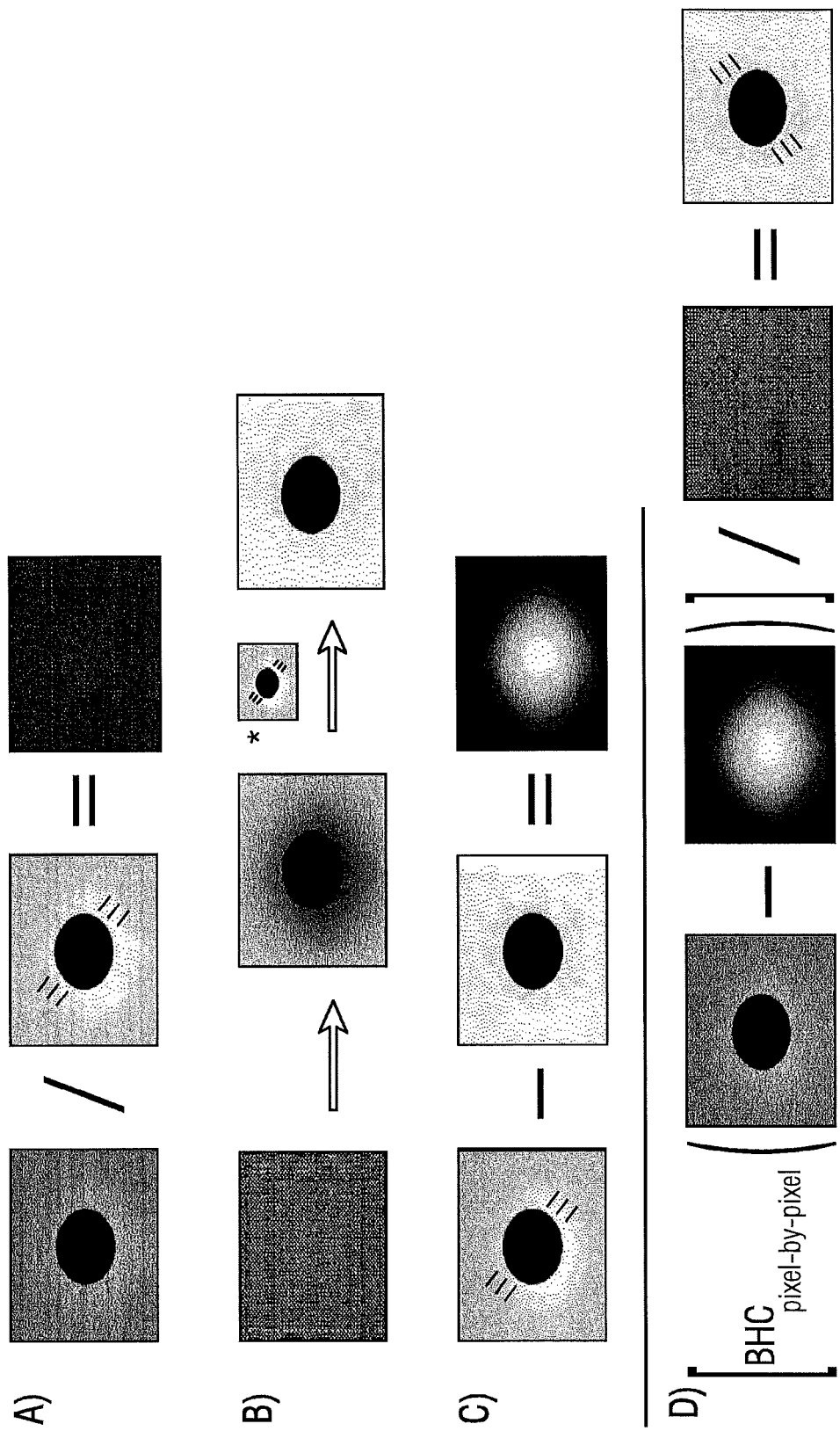
FIGS. 6A to 6D show the second exemplary embodiment of the proposed method for calculating a scatter-corrected projection.

FIGS. 6A to 6D show the second exemplary embodiment of the proposed method for calculating a scatter-corrected projection. According to this exemplary embodiment, in contrast to the first exemplary embodiment, an approximated modulator-free overall image is used instead of a modulator-free overall image. With this approximated modulator-free overall image the high image frequencies caused by object edges and other high-contrast object details can now be divided out in a subsequent step. This is illustrated in FIG. 6A. The modulated projection image, which is in particular downsampled, is therefore divided by the approximated modulator-free overall image, thereby yielding the ratio of measured modulation strength of the primary signal to the overall signal strength as result. This division by the approximated modulator-free overall image replaces the "boundary detection" step of U.S. Pat. No. 7,463,712 B2.

This modulation image freed of object image frequencies is then high-pass filtered in the Fourier domain, as a result of which the low-frequency scatter component is removed and subsequently demodulated accordingly by multiplication in the space domain by a modulator projection without object. This is illustrated in FIG. 6B. The above-performed division by the approximated modulator-free overall image is reversed after the demodulation step by a corresponding multiplication of the approximated modulator-free overall image by the reconstructed primary image. This is illustrated in FIG. 6B.

FIG. 6C shows that the approximated modulator-free overall image is used to obtain the scatter image by a subtraction of the reconstructed primary image performed thereby. This is illustrated in FIG. 6C.

The following method according to FIG. 6D largely corresponds to the first exemplary embodiment.

According to the second exemplary embodiment, in contrast to the first exemplary embodiment, a CT projection is generated per angle rotation increment of the object, such that averaging according to the first exemplary embodiment is dispensed with.

Figure 7:
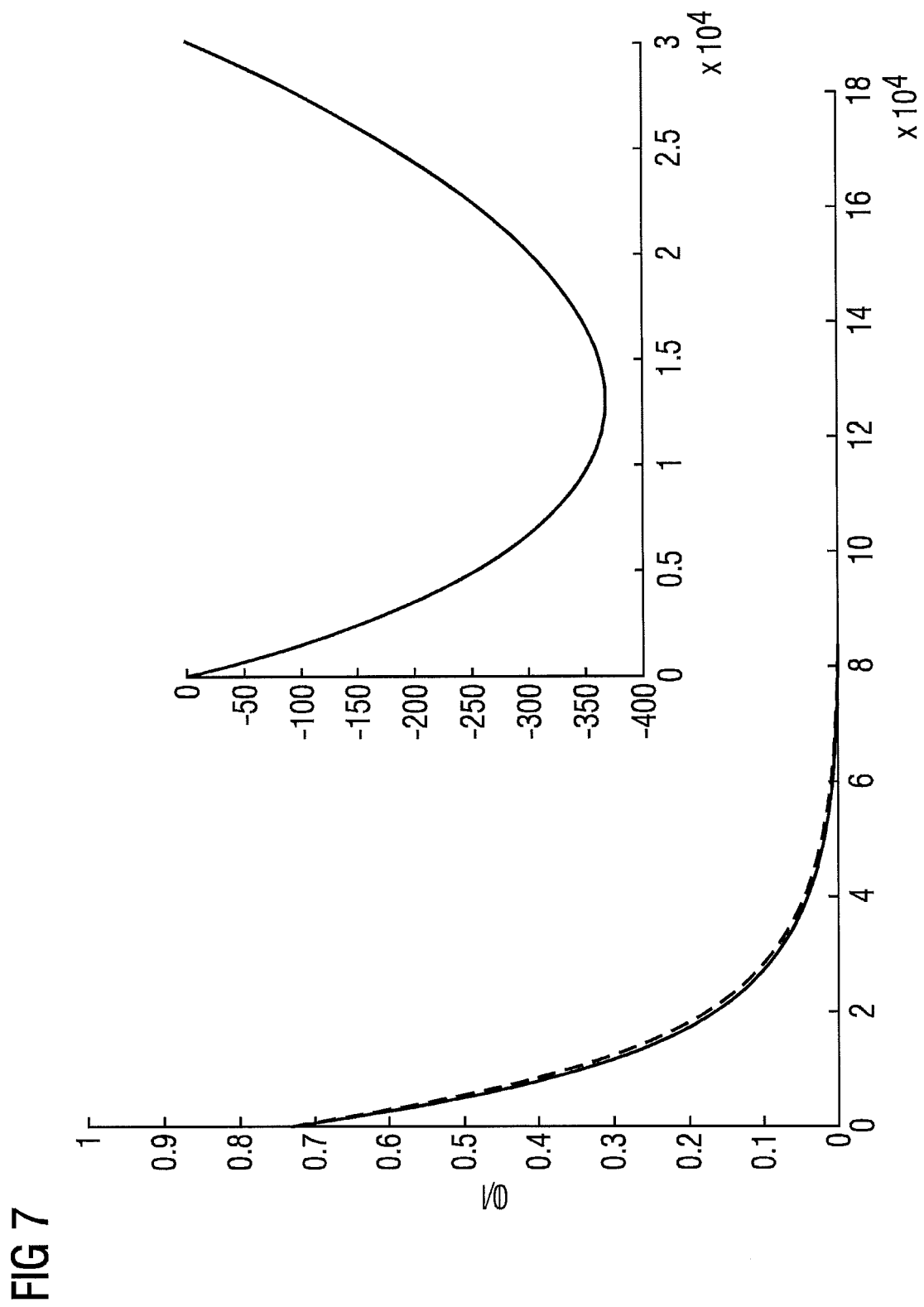
FIG. 7 shows an exemplary embodiment of a correction of beam hardening effects.

FIG. 7 shows an exemplary embodiment of a correction of beam hardening effects, also referred to simply as beam hardening. A simple beam hardening correction is carried out for dark fields, such a correction already being applied in a similar manner for conventional CT, though in that case for complete CT projections.

In the case of primary modulation, a more severe beam hardening effect occurs at the positions of the dark fields, since here the additional material, which can be for example copper or tungsten, causes an additional hardening of the beam which does not occur in the case of the light fields.

By a simple simulation it is possible to simulate theoretically exact attenuation curves for specific recording parameters (see also [1]). A well-known restriction of this method is that in the subsequently described correction the theoretical exactness applies only to monomaterials, i.e. only to objects to be recorded that are formed of one material, which can be for example aluminum. If objects is formed of a plurality of materials, referred to as multimaterials, are examined, a more or less great discrepancy exists in respect of the hardening effects actually occurring.

FIG. 7 shows two attenuation curves $I/I_0$ for the example of the following recording parameters: tube voltage 200 kV, tube-side preamplifier of 2 mm copper and object material aluminum. In this case the two curves show the ratio of the recorded signal to the overall signal, a normalization to 1 having been performed in each case. The ratio of the recorded signal to the overall signal is plotted against the increasing radiation penetration depth through an aluminum wedge. In the left-hand graph the lower curve shows the case of the light fields, in which the prefiltering of the spectrum actually includes only 2.0 mm copper. The upper curve, in contrast, depicts the case of the dark fields, where an overall filter, formed of 2.7 mm copper, is assumed. In other words, in addition to the tube-side prefilter of 2.0 mm thickness, the additional material of the modulator in the dark fields, in this case 0.7 mm copper, is taken into account.

The input intensities, in other words the intensities that are present after the modulator, but before the object, are smaller for the dark fields than for the light fields. Nonetheless, the spectra of the radiation behind the dark fields are on average more energy-rich, i.e. more severely hardened, than the corresponding spectra behind the light fields. Because of this difference between the spectra, the radiation behind the dark fields penetrates the following object material more effectively, and moreover relatively, i.e. referred to the same input intensity. This influencing factor is subsequently taken into account in that for the dark fields this effect is compensated by calculation.

The result for the more strongly filtered 2.7 mm Cu spectrum (upper curve) is a smaller attenuation, considered relatively, than with a more weakly filtered 2.0 mm Cu spectrum (lower curve).

According to a first embodiment variant, a beam hardening correction is performed prior to the scatter estimation. The dark fields of the modulated projection image are corrected for beam hardening in the downsampling step, i.e. the value UncorrVal (m, n) measured in a dark field (m, n) is corrected by a value corrVal, which is calculated as follows:

(1)corr$Val(m,n)$=$BHC$[Uncorr$Val(m,n)$−ApproxScatter$Val(m,n)$]+ApproxScatter$Val(m,n)$ Firstly, an approximated scatter value ApproxScatterVal (M,n), which is generated from the most recently calculated scatter image of the preceding projection, is subtracted from the measured value UncorrVal (m, n). This value is searched for in the attenuation curve for the dark fields (upper curve); it corresponds to a certain radiation penetration depth. A corresponding attenuation value for the light fields (lower curve) can now be found at this radiation penetration depth. This step is represented in the equation as function BHC[.]. Finally, the approximated scatter signal ApproxScatterVal (m, n) is also added to said beam-hardening-corrected value once again. This means that theoretically the beam hardening effect is fully compensated for the treated dark field (m, n).

In addition to the attenuation curves in a coordinate system with radiation-penetrated aluminum depth of arbitrary unit along the abscissa and $I/I_0$ as normalized projection intensity along the ordinate, FIG. 7 shows a second graph which indicates the correction values for the dark fields, i.e. the difference between the two above-described attenuation curves, in grayscale values versus an original grayscale value in a dark field. Analogously it is also possible from the second graph, starting from an original grayscale value in a dark field, to correct this by subtracting the correction value.

According to another advantageous embodiment variant, the correction of beam hardening effects can also be carried out after the scatter estimation and prior to the division by the pure modulator image. Toward that end the following steps must also be performed after the scatter estimation in order to obtain a fully corrected CT projection. The just calculated scatter image is subtracted from the original modulated CT projection. This is illustrated in FIGS. 3D and 6D. A beam hardening correction is then carried out pixel by pixel for the dark fields, as described in conjunction with formula (1). In this case it is taken into account for each pixel individually, how much additionally hardening material is present due to the modulator or modulator field. According to the exemplary embodiment this is between 0.0 and 0.7 mm of additional copper. In this way, when a cone-beam computed tomography system is used, the boundary pixels of the dark fields can likewise be optimally corrected, for with such a system geometry the boundaries of the dark fields are not sharply delimited, in particular for non-centrally located fields, but rather have a gradual grayscale value progression.

Figure 8:
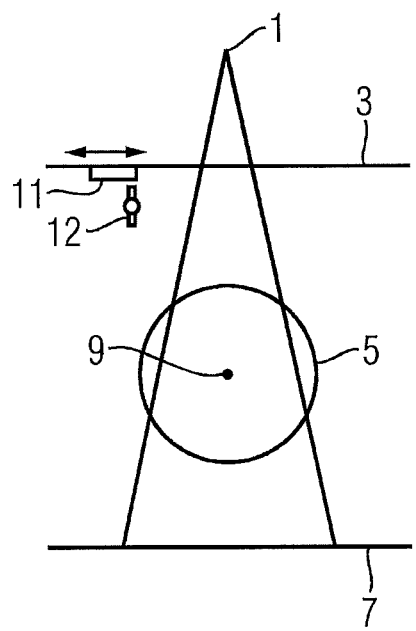
FIG. 8 shows an exemplary embodiment of a proposed device.

FIG. 8 shows an exemplary embodiment of the proposed device. X-ray radiation, represented as a triangle, of a primary x-ray source 1 passes through a modulator field 3 having a repetitive pattern of areas with different x-ray radiation attenuation. The radiation then passes through an object 5 that is to be imaged and is positioned so as to be rotatable about an axis of rotation 9. The result is an original amplitude-modulated projection on a detector 7.

Figure 9:
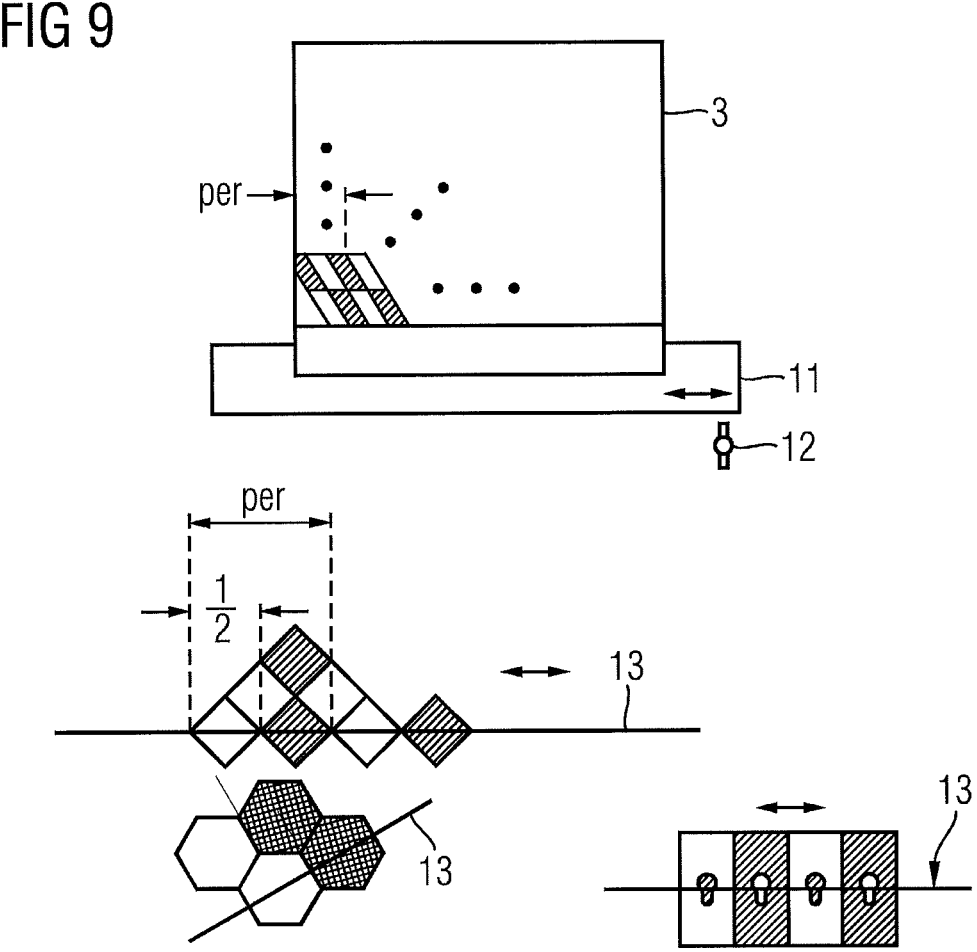
FIG. 9 shows exemplary embodiments of a proposed modulator field.

FIG. 9 shows exemplary embodiments of the proposed modulator field 3 from the direction of the primary x-ray source 1. A linear motor 12 moves a linear stage 11, which positions the modulator field 3. The modulator field 3 contains a repetitive pattern of areas having two different x-ray radiation attenuation coefficients. A first half of the repeating pattern is congruent with a second half, wherein mutually congruent areas of the two halves have mutually opposite x-ray radiation attenuation coefficients, the pattern is repeated along at least one repetition line 13, and a length of the pattern along the repetition line 3 corresponds to a period length per. FIG. 9 shows that in a displacement movement of the modulator field 3 from a first position to a second position along the repetition line 13 by, for example, half a period length, modulator field areas having small x-ray beam attenuation coefficients and in comparison therewith modulator field areas having relatively large x-ray beam attenuation coefficients are reciprocally interchanged. According to the present application, all patterns that provide the above-described interchange are possible in principle. Patterns including polygons are particularly suitable. FIG. 9 shows exemplary embodiments of modulator field patterns, such as parallelograms, rhombuses and hexagons for example. When polygons are used it is furthermore possible to use halves of the pattern that have arbitrary shapes inside the polygons in each case.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

The invention claimed is:

1. A method for correcting artifacts in an x-ray projection of an object, comprising:
    passing x-ray radiation of a primary x-ray source through a modulator field having a repetitive pattern of modulator field areas with different x-ray radiation attenuation, the modulator field producing amplitude-modulated radiation, which is passed through the object to produce an amplitude-modulated projection that is recorded by a detector;
    performing a moving operation to move the x-ray source, the object and the detector relative to the modulator field, from first relative positions to second relative positions, the moving operation reciprocally interchanging modulator field areas having a relatively small x-ray radiation attenuation coefficient with modulator field areas having a relatively large x-ray radiation attenuation coefficient such that first and second original amplitude-modulated projections of the object are generated in the first and second relative positions, respectively;
    calculating first and second scatter images associated with the first and second original amplitude-modulated projections, respectively; and
    using the first and second scatter images to remove scatter contained in the first and second original amplitude-modulated projections.

2. The method as claimed in claim 1, wherein
    in order to calculate the first and second scatter images, a modulator-free overall image is constructed by combining the first and second original amplitude-modulated projections, and the combining uses only projection image fields that were generated by radiation passing through modulator field areas having the relatively small x-ray radiation attenuation coefficient.

3. The method as claimed in claim 2, wherein in order to calculate the first and second scatter images, downsampling is performed before the modulator-free overall image is constructed.

4. The method as claimed in claim 3, wherein
downsampling produces first and second downsampled amplitude-modulated projections, and
in order to calculate the first and second scatter images, high image frequencies caused due to high-contrast object details are removed from the first and second original amplitude-modulated projections, respectively by division of the first and second downsampled amplitude-modulated projections by the modulator-free overall image.

5. The method as claimed in claim 3, wherein in order to calculate the first and second scatter images, respectively, the first and second original amplitude-modulated projections are:
high-pass filtered in a frequency domain in order to remove a low-frequency scatter signal component;
demodulated in a space domain by multiplication by a respective modulator field projection without the object and then low-pass filtered; and thereafter
multiplied by the modulator-free overall image in order to provide first and second demodulated primary images, respectively.

6. The method as claimed in claim 5, wherein
in order to calculate the first and second scatter images respectively, the first and second demodulated primary images are subtracted from the modulator-free overall image.

7. The method as claimed in claim 6, wherein
in order to provide a scatter-corrected projection, the first and second scatter images are subtracted from the first and second original amplitude-modulated projections, respectively.

8. The method as claimed in claim 7, wherein in order to provide an additionally modulator-field-corrected projection, the scatter-corrected projection is divided by the modulator field projection without the object.

9. The method as claimed in claim 8, wherein
for beam hardening correction, for a projection image field that was generated by radiation passing through an area of the modulator field having the relatively large x-ray radiation attenuation coefficient, an approximated scatter value is subtracted in each case from a measured uncorrected intensity value, this difference corresponding to a first intensity value which is assigned by an associated intensity attenuation curve of an associated radiation-penetrated object depth, this is assigned by an intensity attenuation curve for a projection image field that was generated by radiation passing through an area of the modulator field having the relatively small x-ray radiation attenuation coefficient to a second intensity value to which the approximated scatter value is added again, and
the beam hardening correction is carried out prior to dividing the scatter-corrected projection by the modulator field projection without the object.

10. The method as claimed in claim 7, wherein a scatter-corrected or scatter- and modulator-field-corrected projection is generated for each of the first and the second relative positions with subsequent averaging in order to increase a signal-to-noise ratio.

11. The method as claimed in claim 1, wherein
the modulator field is moved back and forth between the first and second relative positions, and
after every second projection, the x-ray source, the modulator field and the detector are rotated relative to the object about an axis of rotation in one rotational direction by a rotation angle increment.

12. The method as claimed in claim 11
the modulator field is moved back and forth between the first second relative positions,
after each projection, the x-ray source, the modulator field and the detector are rotated relative to the object about an axis of rotation in one rotational direction by a rotation angle increment, and
in order to calculate the first and second scatter images, an approximated modulator-free overall image is used in which projection image fields of a current original projection of the object are combined with interpolated projection image fields of a preceding and a succeeding original projection of the object, with only projection image fields being used that were generated by radiation passing through areas of the modulator field having the relatively small x-ray radiation attenuation coefficient.

13. The method as claimed in claim 1, wherein for beam hardening correction, for a projection image field that was generated by radiation passing through an area of the modulator field having the relatively large x-ray radiation attenuation coefficient, an approximated scatter value is subtracted in each case from a measured uncorrected intensity value, this difference corresponding to a first intensity value which is assigned by an associated intensity attenuation curve of an associated radiation-penetrated object depth, this is assigned by an intensity attenuation curve for a projection image field that was generated by radiation passing through an area of the modulator field having the relatively small x-ray radiation attenuation coefficient to a second intensity value to which the approximated scatter value is added again.

14. The method as claimed in claim 13, wherein the approximated scatter value was determined from a calculated scatter image of a preceding original projection.

15. The method as claimed in claim 13, wherein
in order to calculate the first and second scatter images, a modulator-free overall image is constructed by combining the first and second original amplitude-modulated projections,
the combining uses only projection image fields that were generated by radiation passing through modulator field areas having the relatively small x-ray radiation attenuation coefficient,
downsampling is performed before the modulator-free overall image is constructed, and
the beam hardening correction is carried out during the downsampling.

16. A device for correcting artifacts in an x-ray projection of an object, wherein x-ray radiation of a primary x-ray source passes through a modulator field containing a repetitive pattern of areas having different x-ray radiation attenuation, is amplitude-modulated thereby, then passes through the object to produce an image that is recorded by a detector, where it is recorded and a scatter image is calculated therefrom which is separated from an original amplitude-modulated projection, wherein the modulator field has a repeating pattern, a first half of which is congruent with a second half, mutually congruent areas of the halves have mutually opposite x-ray radiation attenuation coefficients, the pattern is repeated along at least one repetition line, and a length of the pattern along the repetition line corresponds to a period length, the device comprising:

a shifting apparatus for moving the x-ray source, the object and the detector relative to the modulator field from first relative positions to a second relative positions along the repetition line by an uneven multiple of a half period length in each case such that modulator field areas having a relatively low x-ray radiation attenuation coefficient and modulator field areas having a relatively large x-ray radiation attenuation coefficient are reciprocally interchanged; and a processor calculating the scatter image.

17. The device as claimed in claim 16, wherein the device is a computed tomography system.

18. The device as claimed in claim 17, wherein the computed tomography system is a cone-beam computed tomography system.

19. The device as claimed in claim 18, wherein the computed tomography system is a cone-beam computed tomography system for industrial applications.

20. The device as claimed in claim 16, wherein the shifting apparatus and a rotation apparatus for rotating the object about an axis of rotation in one rotational direction by respective rotation angle increments are synchronized with one another.

21. The device as claimed in claim 16, wherein the pattern of the modulator field includes polygons which generate no checkerboard pattern.

22. The device as claimed in claim 21, wherein the halves of the pattern each have arbitrary shapes inside the polygons.

23. The device as claimed in claim 16, wherein the halves of the pattern each include triangles, parallelograms, rhombuses, hexagons and octagons.

* * * * *